US009012438B2

(12) United States Patent  
Pinchera et al.

(10) Patent No.: US 9,012,438 B2
(45) Date of Patent: Apr. 21, 2015

(54) 3,5,3'-TRIIODOTHRONINE SULFATE AS THYROMIMETIC AGENT AND PHARMACEUTICAL FORMULATIONS THEREOF

(76) Inventors: Aldo Pinchera, Pisa (IT); Ferruccio Santini, Carrara (IT)

(*) Notice: Subject to any disclaimer, the term of this patent is extended or adjusted under 35 U.S.C. 154(b) by 136 days.

(21) Appl. No.: 10/532,447

(22) PCT Filed: Nov. 11, 2003

(86) PCT No.: PCT/EP03/12584
§ 371 (c)(1),
(2), (4) Date: Apr. 22, 2005

(87) PCT Pub. No.: WO2004/043452
PCT Pub. Date: May 27, 2004

(65) Prior Publication Data
US 2005/0272816 A1 Dec. 8, 2005

(30) Foreign Application Priority Data

Nov. 13, 2002 (IT) .............................. MI2002A2394

(51) Int. Cl.
*A61K 31/185* (2006.01)
*A61K 31/198* (2006.01)
*A61K 9/20* (2006.01)
*A61K 31/197* (2006.01)

(52) U.S. Cl.
CPC ................ *A61K 31/198* (2013.01); *A61K 9/20* (2013.01); *A61K 31/197* (2013.01)

(58) Field of Classification Search
CPC ..... A61K 31/198; A61K 31/197; A61K 9/20; C07D 495/04; C07F 1/04
USPC ........................................................ 514/310
See application file for complete search history.

(56) References Cited

U.S. PATENT DOCUMENTS

| | | | |
|---|---|---|---|
| 2,970,165 A | 1/1961 | Raymond et al. | |
| 2,993,928 A | 7/1961 | Razdan et al. | |
| 3,313,839 A | 4/1967 | Rozzi | |
| 4,254,095 A * | 3/1981 | Fisher et al. | 436/513 |
| 5,116,828 A * | 5/1992 | Miura et al. | 514/171 |
| 5,158,978 A | 10/1992 | Rubin | |
| 5,225,204 A | 7/1993 | Chen et al. | |
| 5,272,078 A * | 12/1993 | Larsen et al. | 435/189 |
| 5,324,522 A | 6/1994 | Krenning et al. | |
| 5,753,254 A | 5/1998 | Khan et al. | |
| 5,955,105 A | 9/1999 | Mitra et al. | |
| 5,958,979 A | 9/1999 | Lahr et al. | |
| 6,056,975 A | 5/2000 | Mitra et al. | |
| 6,406,667 B1 | 6/2002 | Singh et al. | |
| 6,555,581 B1 | 4/2003 | Franz et al. | |
| 6,599,942 B1 * | 7/2003 | Kukkola | 514/563 |
| 6,646,007 B1 | 11/2003 | Schreder et al. | |
| 6,740,680 B1 * | 5/2004 | Danforth, Jr. et al. | 514/570 |
| 6,855,333 B1 | 2/2005 | Spireas | |
| 6,979,462 B1 | 12/2005 | Spireas | |
| 7,052,717 B2 | 5/2006 | Hanshew et al. | |
| 7,067,148 B2 | 6/2006 | Franz et al. | |
| 7,101,569 B2 | 9/2006 | Franz et al. | |
| 7,163,918 B2 * | 1/2007 | Piccariello et al. | 514/5 |
| 7,691,411 B2 | 4/2010 | Di Martino et al. | |
| 7,723,390 B2 | 5/2010 | Garavani et al. | |
| 8,008,349 B2 | 8/2011 | Schreder et al. | |
| 2001/0051657 A1 * | 12/2001 | Chiang et al. | 514/562 |
| 2002/0076827 A1 * | 6/2002 | Salhanick et al. | 436/501 |
| 2003/0050344 A1 | 3/2003 | Garavani et al. | |
| 2003/0198668 A1 | 10/2003 | Franz et al. | |
| 2004/0063611 A1 | 4/2004 | Schreder et al. | |
| 2004/0156893 A1 | 8/2004 | Klein et al. | |
| 2005/0249801 A1 | 11/2005 | Spireas | |
| 2005/0266570 A1 | 12/2005 | Carey et al. | |
| 2005/0272816 A1 | 12/2005 | Pinchera et al. | |
| 2007/0014851 A1 | 1/2007 | Burghart et al. | |
| 2007/0276042 A1 | 11/2007 | Gant et al. | |
| 2008/0003284 A1 | 1/2008 | Franz et al. | |
| 2008/0193527 A1 | 8/2008 | Ruiz Amenos et al. | |
| 2010/0136109 A1 | 6/2010 | Ross et al. | |
| 2011/0064773 A1 | 3/2011 | Leverve et al. | |
| 2011/0245342 A1 | 10/2011 | Pinchera et al. | |

FOREIGN PATENT DOCUMENTS

| | | | |
|---|---|---|---|
| CA | 2333193 A1 | 11/1999 | |
| CA | 2523079 A1 | 11/2004 | |
| CN | 1711079 A | 12/2005 | |
| DE | 19541128 A1 | 4/1997 | |
| EP | 0550108 A1 | 7/1993 | |
| EP | 0466909 B1 | 6/1995 | |
| EP | 0732920 B1 | 10/2003 | |
| EP | 1291021 A2 | 12/2003 | |

(Continued)

OTHER PUBLICATIONS

Herfindal et al. In: Clinnical Pharmacy and Therapeutics. 1992, pp. 289-291.*
Mol et al. Synthesis and some properties of sulfate esters and sulfamates of iodothyronines. Endocrinology. 1985; 117(1):1-7, abstract only.*
Bunevicius et al. Effects of thyroxine as compared with thyroxine plus triiodothyronine in patients with hypothydroidism. New England Journal of Medicine. 1999; 340(6):424-429; electronic pp. 1-12.*
Wu et al. (Wu et al. Thyroxine sulfate is a major thyroid hormone metabolite and a potential intermediate in the monodeiodination pathways in fetal sheep. Endorcrinology. 1992;131(4):1751-1756.*
Remington: The Science and Practice of Pharmacy, 19th edition, 1995, Alfonso R. Gennaro, Ed., Chapter 92, Oral Solid Dosage Forms by Edward Rudnic, PhD, pp. 1615-1649.*
LoPresti Jonathan S. et al: "Characteristics of 3,5.3'-Trlodothyronine Sulfate Metabolism in Euthyroid Man" Journal of Clinical Endocrinology and Metabolism, vol. 73, No. 4. 1992, pp. 708-709.

(Continued)

Primary Examiner — Kortney L Klinkel
(74) Attorney, Agent, or Firm — M. Caragh Noone

(57) ABSTRACT

The invention regards the use of triiodothyronine sulfate, commonly named $T_3S$, as a medicament having thyromimetic activity for the treatment of pathologies due to organic deficiency of triiodothyronine ($T_3$), as such or in association with thyroxine ($T_4$), and pharmaceutical formulations thereof.

16 Claims, No Drawings

(56) References Cited

FOREIGN PATENT DOCUMENTS

| EP | 1433478 A1 | 6/2004 |
|---|---|---|
| EP | 1560575 B1 | 9/2006 |
| EP | 1322294 B1 | 12/2007 |
| JP | 63-079824 A | 4/1988 |
| JP | 5-255081 A | 10/1993 |
| JP | 7-116031 A | 12/1995 |
| WO | 91/11181 A1 | 8/1991 |
| WO | 95/20953 A1 | 8/1995 |
| WO | 97/17951 A2 | 5/1997 |
| WO | 03/007994 A2 | 1/2003 |
| WO | 02/28364 A2 | 4/2004 |
| WO | 2004/071432 A2 | 8/2004 |
| WO | 2005/004849 A2 | 1/2005 |
| WO | 2008/129303 A2 | 10/2008 |
| WO | 2008/138995 A1 | 11/2008 |

OTHER PUBLICATIONS

Santini Ferruccio et al: "Thyromimetic effects of 3,5,3'-triiodothyronine sulfate in hypothyroid rats" Endocrinology, vol. 133, No. 1, 1993, pp. 105-110, XP002272821.
Chopra I J et al: "Demonstration of thyromimetic effects of 3,5,3'-triiodothyronine sulfate (T3S) in euthyroid rats" Thyroid 1996. United States, vol. 6, No. 3, 1996, pp. 229-232, XP009027310.
PCT Search Report for PCT/EP03/12584, mail date Mar. 25, 2004.
Office Action for U.S. Appl. No. 13/755,279, mail date Dec. 4, 2013.
The Code of Federal Regulations (Title 21-Food and Drugs, vol. 3, Apr. 1, 2012, §184.1328 glyceryl behenate).
Application, National Phase of PCT/EP2012/056274 (WO2012/1367671A1), U.S. Appl. No. 14/110,237, filed Oct. 7, 2013, with Preliminary Amendment.
U.S. Appl. No. 14/249,542, Continuation of U.S. Appl. No. 14/110,237, filed Apr. 10, 2014, with Preliminary Amendment, filing date, Apr. 14, 2014.
Feigenbaum, J. et al., "Simplified Method for the Preparation of Aromatic Sulfuric Acid Esters", Journal of the American Chemical Society, American Chemical Society, Washington DC, vol. 63, 1941, pp. 3259-3530, XP-002522192, ISSN: 0002-7863.
Mol, Jan et al., "Synthesis and some properties of sulfate esters and sulfamates of iodothyronines", Endocrinology, vol. 117, No. 1, 1986, The Endocrine Society, pp. 1-7, XP009153115.
PCT International Preliminary Examination Report for PCT/EP2003/012584, mail date Feb. 24, 2005.
PCT International Search Report and Written Opinion for PCT/EP2012/056274, mail date Jun. 14, 2012.
PCT International Search Report and Written Opinion for PCT/EP2012/056274, mail date Aug. 8, 2012.
PCT Written Opinion of the International Preliminary Examining Authority for PCT/EP2012/056274, mail date Mar. 12, 2013.
PCT Written Opinion of the International Preliminary Examining Authority for PCT/EP2012/056274, mail date May 31, 2013.
PCT International Preliminary Report on Patentability for PCT/EP2012/056274, mail date Aug. 27, 2013.
Chopra, Inder J., "Nature, Sources and Relative Biologic Significance of Circulating Thyroid Hormones", Braverman LE., Utiger RD (eds) The Normal Thyroid, Lippincott, Philadelphia USA, 1991, pp. 126-143.
De Herder, WW et al., "Rapid and Bacteria-Dependent In Vitro Hydrolysis of Iodothyronine-Conjugates by Intestinal Contents of Humans and Rats", Medical Biology, vol. 64, 1986, pp. 31-35.
Kung, Mei-Ping et al., "Desulfation of 3,5,3'-Triiodothyronine Sulfate by Microsomes from Human and Rat Tissues", Endocrinology, vol. 122, No. 4, 1988, pp. 1195-1200.
Mol, Jan A. et al., "Rapid and Selective Inner Ring Deiodination of Thyroxine Sulfate by Rat Liver Deiodinase", Endocrinology, vol. 117, No. 1, 1986, pp. 8-12.
Otten, M.H. et al., "Sulfation Preceding Deiodination of iodothyronines in Rat Hepatocytes", Science, vol. 221, 1983, pp. 81-83.
Santini, Ferruccio et al., "A Study of Metabolism of Deaminated and Sulfoconjugated Iodothyronines by Rat Placental Iodothyronine 5-Monodeiodinase", Endocrinology, vol. 131, No. 4, 1992, pp. 1689-1694.
Santini, Ferruccio et al., "Evidence for the role of the type III-iodothyronine deiodinase in the regulation of 3,5,3'-triiodothyronine content in the human central nervous system", European Journal of Endocrinology, vol. 144, 2001, pp. 577-583, ISSN 0804-4643.
Santini, F. et al., "A Study of the Serum 3,5,3'-Triiodothyronine Sulfate Concentration in Normal and Hypothyroid Fetuses at Various Gestational Stages", Journal of Clinical Endocrinology and Metabolism, vol. 76, No. 6, 1993, pp. 1583-1587.
Santini, Ferruccio et al., "Serum Iodothyronines in the Human Fetus and the Newborn: Evidence for an Important Role of Placenta in Fetal Thyroid Hormone Homeostasis", Journal of Clinical Endocrinology and Metabolism, vol. 84, No. 2, 1999, pp. 493-498.
Santini, Ferruccio et al., "Metabolism of 3,5,3'-Triiodothyronine Sulfate by Tissues of the Fetal Rat: A Consideration of the Role of Desulfation of 3,5,3'-Triiodothyronine Sulfate as a Source of T3", Pediatric Research, vol. 31, No. 6, 1992, pp. 541-544.
Spaulding, Stephen W. et al., "Studies on the Biological Activity of Triiodothyronine Sulfate", Journal of Clinical Endocrinology and Metabolism, vol. 74, No. 5, 1992, pp. 1062-1067.
AACE Thyroid Guidelines, "American Association of Clinical Endocrinologists Medical Guidelines for Clinical Practice For the Evaluation and Treatment of Hyperthyroidism and Hypothyroidism: AACE Thyroid Task Force", Endocrine Practice, vol. 8, No. 6, Nov.-Dec. 2002, pp. 457-469.
Biondi, Bernadette et al., "Combination Treatment with T4 and T3: Toward Personalized Replacement Therapy in Hypothyroidism?", J Clin. Endocrinol. Metab, Special Feature Clinical Review, 2012, vol. 97, No. 7, doi:10.1210/jc.2011-3399, The Endocrine Society, pp. 1-16.
Chalmers, J.R. et al., "The Synthesis of Thyroxine and Related Substances. Part V. A Synthesis of L-Thyroxine from L-Tyrosine", 1949, pp. 3424-3433, http://pubs.rsc.org|doi:10.1039/JR9490003244.
Chopra, Inder J. et al., "A Radioammunoassay for Measurement of 3,5,3'-Triiodothyronine Sulfate: Studies in Thyroidal and Nonthyroidal Diseases, Pregnancy, and Neonatal Life", Journal of Clinical Endocrinology and Metabolism, 1992, vol. 75, No. 1, pp. 189-194, The Endocrine Society.
Escobar-Morreale, Hector F. et al., "Reivew: Treatment of Hypothyroidism with Combinations of Levothyroxine plus Liothyronine", The Journal of Clinical Endocrinology & Metabolism, 2005, vol. 90, No. 8, pp. 4946-4954, The Endocrine Society, doi: 10.1210/jc.2005-0184.
Goodman & Gilman's "The Pharmacological Basis of Therapeutics", Ninth Edition, Chapter 1 Pharmacokinetics, McGraw-Hill, 1996, p. 5.
Goodman & Gilman's "The Pharmacological Basis of Therapeutics", Ninth Edition, Section XIII Hormones and Hormone Antagonists, McGraw-Hill, 1996, pp. 1394-1395.
Guillo, Damiano et al., "Levothyroxine Monotherapy Cannot Guarantee Euthyroidism in All Altyreotic Patients", PLOS One, 2011, vol. 6, Issue 8, e22552, www.plosone.org, pp. 1-7.
Harrison's Principles of Internal Medicine, 16th edition (Manual), 2005, McGraw-Hill Companies, Inc., p. 2112.
Hemmila, Ilkka et al., "Europium as a Label in Time-Resolved Immunofluorometric Assays", Analytical Biochemistry, 1984, vol. 137, pp. 335-343, Academic Press Inc.
Martindale "The Complete Drug Reference", 36th Edition (Manual), 2009, The Pharmaceutical Press, pp. 2167, 2171-2172, 2174.
Mol, Jan et al., "Synthesis and some properties of sulfate esters and sulfamates of iodothyronines", Endocrinology, vol. 117, No. 1, 1985, The Endocrine Society, pp. 1-7, XP009153115.
"Orange Book: Approved Drug Products with Therapeutic Equivalence Evaluations: query on Levothyroxine", FDA U.S. Food & Drug Administration. p. 1-14, Orange Book data updated through May 2012; Patent and Generic Drug Product Data Last Updated Jul. 2, 2012.
"Orange Book: Approved Drug Products with Therapeutic Equivalence Evaluations: query on Liothyronine", FDA U.S. Food & Drug Administration. p. 1-3, Orange Book data updated through May 2012; Patent and Generic Drug Product Data Last Updated Jul. 2, 2012.

(56) References Cited

OTHER PUBLICATIONS

Roberts, Caroline G.P. et al., "Hypothroidism", Seminar, The Lancet, 2004, vol. 363, pp. 793-803.
Roche, Jean et al., "Hepatic sulphate conjugation of 3,5,3'-triiodo-L-thyronine and the presence of a sulphuric ester of this hormone in bile and plasma", 1959, vol. 33, pp. 461-469.
Rohm and Haas, "Amberlite™ XAD™ 1600N: Macroreticular Polymeric Adsorbent", Mar. 2005, total of 4 pages.
Santini, Ferruccio et al., Steady-State Serum T3 Concentrations for 48 Hours Following the Oral Administration of a Single Dose of 3,5,3'-Triiodothyronine Sulfate (T3S), Endocrine Practice, 2014, vol. 20, No. 7, pp. 680-689.
The Merck Manual of Diagnosis and Therapy, 17th Edition, (Manual), 1999, pp. 92-95.
Visser, Theo J., "Role of sulfation in thyroid hormone metabolism", Chemico-Biological Interactions, vol. 92, 1994, pp. 293-303, Elsevier Science Ltd.
Wiersinga, Wilmar M., "Thyroid Hormone Replacement Therapy", Hormone Research, 2001, vol. 56(Suppl 1), pp. 74-81.
Office Action-First for Chinese application No. 200380103057.4, mail date Nov. 10, 2006 (English translation).
Office Action-Second for Chinese application No. 200380103057.4, mail date Jun. 22, 2007 (English translation).
Office Action: Rejection Decision for Chinese application No. 200380103057A, mail date Mar. 28, 2008 (English translation).
Office Action: Notification of Reexamination for Chinese application No. 200380103057.4, mail date Apr. 8, 2009 (English translation).
Office Action-First for Chinese application No. 200810135762.7, mail date Jun. 10, 2010 (English translation).
Office Action-Second for Chinese application No. 200810135762.7, mail date Oct. 25, 2011 (English translation).
Office Action: Rejection Decision for Chinese application No. 200810135762.7, mail date Aug. 3, 2012 (English translation).
Office Action: Notification of Reexamination for Chinese application No. 200810135762.7, mail date Aug. 1, 2013 (English translation).
Office Action—First for Chinese application No. 201280023319.5, mail date Oct. 20, 2014 (English translation).
Office Action for Japanese application No. 2004-550983, mail date Jan. 19, 2010 (English translation).
Office Action: Decision Refusal for Japanese application No. 2004-550983, mail date Aug. 24, 2010 (English translation).
Office Action: PreTrial Re-Examination for Japanese application No. 2004-550983, mail date Jan. 31, 2012 (English translation).
Office Action: Trial Decision for Japanese application No. 2004-550983, mail date May 21, 2013 (English translation).
Office Action for Japanese application No. 2010-288189, mail date Jan. 8, 2013 (English version).
Faber, J., et al., "Urinary Excretion of Free and Conjugated 3',5'-Diiodothyronine and 3,3'-Diiodothyronine", Journal of Clinical Endocrinology and Metabolism, 1981, vol. 53, No. 3, pp. 587-593, The Endocrine Society.
Rooda, Sebo Jan Eelkman et al., "Metabolism of Triiodothyronine in Rat Hepatocytes", Endocrinology, 1989, vol. 125, No. 4, pp. 2187-2197, The Endocrine Society.
Office Action: Notice of Allowance for U.S. Appl. No. 13/755,279, mail date Jan. 30, 2015.
Office Action-First: for Japanese application No. 2014-503150, mail date Feb. 24, 2015 (English translation).
Office Action: Reexamination Decision for Chinese application No. 200810135762.7, mail date Jan. 26, 2015 (English translation).

* cited by examiner

3,5,3'-TRIIODOTHRONINE SULFATE AS THYROMIMETIC AGENT AND PHARMACEUTICAL FORMULATIONS THEREOF

This application is the national stage application of corresponding international application number PCT/EP2003/012584 filed Nov. 11, 2003, which claims priority to and the benefit of the Italian application no. MI2002A002394, filed Nov. 13, 2002, all of which are hereby incorporated by reference.

FIELD OF THE INVENTION

The present invention regards the use of 3,5,3'-triiodothyronine sulfate, usually named triiodothyronine sulfate or $T_3$ sulfate or even better $T_3S$, as an active principle, alone or in combination with thyroxine, in the treatment of pathologies due to organic deficiency of 3,5,3'-triiodothyronine. Accordingly, the same is usable for the preparation of thyromimetic pharmaceutical compositions.

BACKGROUND OF THE INVENTION

A number of iodothyronines are present in blood, which are directly produced by thyroid gland or are the result of peripheral metabolism of other iodothyronines. Among them, 3,5,3'-triiodothyronine (acronym $T_3$) is deemed to be the biological active form of thyroid hormone (TH), because it has shown high affinity for the specific receptors of the same and is normally present in serum at a concentration sufficient for the activation of said receptors.

The main secretion product of thyroid gland in the healthy adult is thyroxine, commonly designated with the acronym $T_4$. It is peripherically converted to its biologically active form, $T_3$ (Ref. 1), through enzymatic removal of an iodine atom from the external aromatic ring of the molecule by both type I and type II 5'-iodothyronine monodeiodinases (type I MD and type II MD, respectively). This metabolic pathway is the main mechanism of endogenous production of $T_3$; on consequence, $T_4$ can properly be considered a pro-hormone. On the other hand, a minor part of $T_3$ is also directly secreted by thyroid. On average, the amount of $T_4$ produced in an adult being of 70 Kg weight every day amounts to 100 µg, while the total production of $T_3$ amounts to around 25 µg. 4-8 µg of $T_3$ out of said 25 µg are directly secreted by thyroid and the remaining ones derive from the peripheral conversion of $T_4$.

$T_3$ undergoes two different metabolic pathways. The main metabolic pathway consists in the partial deiodination of the inner aromatic ring by type III 5-iodothyronine monodeiodinase (type III MD) to give 3,3'-diiodothyronine, which is biologically non-active and is further metabolized through deiodination or sulfoconjugation. The other metabolic pathway regards around 20% of the total amount of $T_3$ produced by the body and brings on sulfoconjugation of $T_3$ to give $T_3S$, which is not able to bond to the thyroid hormones (Ref. 2), thus resulting biologically non-active (Ref. 3).

Contrary to what happens with $T_3$, $T_3S$ is not deiodinated by type III MD. Rather, it resulted to be an excellent substrate for type I MD (Ref. 4), which converts it very quickly into 3,3'-diiodothyronine sulphate. On consequence it has been widespread common knowledge that, in the healthy adult being, sulfoconjugation of $T_3$ to give $T_3S$ represents a way for speeding up the catabolism of $T_3$, so facilitating its biliary and urinary excretion. Actually, it was found that serum levels of $T_3S$, physiologically low in the health adult, are higher when type I MD activity is reduced.

Yet, it has also unexpectedly been found that, just in some body districts and organs, sulfatases exist which, under particular physiological conditions and situations, are able to convert again $T_3S$ into its active form $T_3$ (Ref's. 7-9).

Such enzymes have been described in the intestinal microflora as well as in body tissues like liver, kidneys and nervous central system (Ref. 10).

Recently, it has been found that endogenous $T_3S$ levels in serum are quite high during intrauterine life and as such are kept by the body, i.e. higher than the ones normally found in the adult being, at least until the forth month of postnatal life (Ref. 11). Considering the essential role played by thyroid hormones during growth, in particular as far as nervous central system functions are involved, suppositions have been made about the possibility that, in this tissue, $T_3S$ may also possibly be used by the body as an occasional source of $T_3$, if and when needed, during the first period of life. Studies performed on autoptic specimens of human nervous cerebral tissue post-mortem showed that the amount of $T_3$ in the same results limited by type III MD (Ref. 12). While this enzyme does not attack $T_3S$, it has been surmised that $T_3S$ may exceptionally represent an alternative endogenous source of $T_3$ hormone in those tissues which contain sulfatases able to reconvert $T_3S$ into its active form, just in case a particular need of the hormone arises in said tissues (Ref's. 8, 13).

Further studies have been performed to ascertain the effective role played by $T_3S$ during production and metabolism of thyroid hormones. Said studies have recently demonstrated that it shows thyromimetic effects in hypothyroid rats (Ref. 10) as well as in euthyroid rats (Ref. 14). In both cases $T_3S$ has shown a potency of around one fifth that of $T_3$. Moreover both treatments with $T_3S$ and with $T_3$ produced a significant reduction of serum levels of thyreotropic hormone (TSH) in euthyroid rats, thus showing to possess similar capability in inhibiting its secretion. On the contrary, in the case of hypothyroid rats, $T_3S$ showed a poor capability of inhibiting TSH secretion when compared to $T_3$. It is well known that TSB is a highly responsive indicator to the functional status of thyroid gland and consents to detect the smallest alterations of its hormonal secretion. Actually, its levels are higher under conditions of reduced thyroid functionality, even in those conditions that are defined as sub-clinical, while they are reduced when an excess of thyroid hormones are present. Accordingly, $T_3S$ seems unexpectedly non-comparable to $T_3$ as far as its capability of inhibition on formation of TSH is involved.

In conclusion, particularly in view of the latest studies, a clear and complete knowledge of the biological role played by $T_3S$ has not yet been reached.

In fact its main, well-grounded and universally accepted, feature is its non-biological activity, i.e. it is a biologically inert metabolite of $T_3$ (Ref's. 2 and 3), and the sulfation pathway is regarded as a metabolic activator of $T_3$ catabolism (Ref. 5).

On the other hand, only in particular tissues and under exceptional critical conditions due to shortage of thyroid hormone in those tissues, it has been shown its potential as an endogenous local source of $T_3$.

As a result, today the skilled technician is still facing a complex, somewhat conflicting, situation, which highlights only some of the biological characteristics of the product and needs more exhaustive in depth studies.

In any case, none of the several documents forming the state-of-the-art discloses, shows or suggests the possibility of using this anomalous metabolite of $T_3$ in therapy. No close prior-art document, either of experimental nature or substantially speculative, either taken alone or in combination with other related documents, suggests the use, or even the potential use of $T_3S$ as a medicament, taken as such or preferably in combination with other thyroid hormones or pro-hormones, like, for example $T_4$. The fact that, only in some specific tissues of the body and under particular, peculiar circumstances, part of $T_3S$ can be reconverted into $T_3$ does not mean, nor implies, nor suggests that it is possible to generalize this feature to the whole organism through exogenous administration of the product. In particular, there is no suggestion that oral administration of the product, even in protected form according to known methods of the pharmaceutical technique, may render it bioavailable also because it is well known that in those districts where suitable sulfatases are not present the same is rapidly metabolized and excreted through the bile and urines.

SUMMARY OF THE INVENTION

It has now unexpectedly been found, and this is one of the aspects of the present invention, that $T_3S$, as such or in association with other thyroid hormones or pro-hormones, preferably $T_4$, and properly formulated according to the desired application, is particularly useful as a medicament to be used in all those pathologies caused by insufficient production by the body of the needed quantities of active thyroid hormones, in particular $T_3$.

DETAILED DESCRIPTION OF THE INVENTION

In fact, it has unexpectedly been found that the administration of $T_3S$, contrary to what known about its normal metabolism, allows to maintain steady levels of $T_3$ in the body for long times (from 12 to 18 hrs) and that results particularly useful in those cases in which it is needed to supplement thyroid hormone in its most active form.

Particularly preferred in the therapy of hypothyroidism, and this is a main aspects of the present invention, is resulted the association of $T_3S$ with $T_4$. The hormonal association which, in theory, should more accurately mime the normal thyroid secretion is represented by a combination of $T_4$ with $T_3$. Actually, pharmaceutical compositions comprising both of said iodothyronines, formulated in proportions similar to the ones of the normal physiologic secretion, have already been tried and marketed. Unfortunately, the oral simultaneous administration of $T_4$ with $T_3$ was not able to reproduce the normal thyroid hormones serum levels, because of pharmacokinetics of $T_3$. In fact, $T_3$ undergoes a very quick absorption and an equally quick elimination after oral administration; its elimination rate is about 20 times higher than the one of $T_4$. For this reason administration of $T_3$ gives raise to a dangerous peak excess in hormone concentration, if compared to the normal physiologic levels, followed by a too much fast drop to sub-physiologic levels. On consequence, today most of the specialised physicians prefer using $T_4$ alone, even if in this way production of $T_3$ only depends on the periferic deiodination of $T_4$, because direct secretion of $T_3$ by thyroid does not exists or is seriously insufficient.

On the contrary, the association of the invention avoids the above problems, because it has unexpectedly been found that, for example, after oral administration, $T_3S$ provides $T_3$ serum levels that increase in a gradual way and keep steady for long periods of time, thus preventing the formation of too much high peaks.

Another unexpected advantage deriving from the use of $T_3S$ in the treatment of pathologies due to organic deficiency of $T_3$ consists in its recently found systemic thyromimetic activity linked to a poor inhibition of TSH secretion. This effect is particularly useful in the case of thyroidectomized patients suffering from thyroid carcinoma, when administration of $T_4$ must be suspended in view of carrying out total body scintigraphy. In such a case administration of $T_3S$ instead of $T_4$ may solve patient's necessity, without interfering with the diagnostic examination.

Another further advantage of $T_3S$ in the therapy of hypothyroidism regards its autolimitation capability. In fact, it is actively deiodinated by type I MD, which, on its part, is stimulated by thyroid hormones. In hypothyroid subjects type I MD activity is reduced; on consequence also $T_3S$ elimination is slowed. As a matter of fact, its effect on the body results greater. On the contrary, in case of over administration, type I MD activity is increased, thus giving more $T_3S$ elimination, i.e. limiting possible undesired collateral effects.

Last but not least, a further advantage of $T_3S$ is represented by the fact that it is a metabolite normally present in the body, usually non-active, i.e. non-toxic. On consequence problems of hypersensitivity or intolerance following its administration are not reasonably predictable.

Accordingly, another main aspect of the present invention regards pharmaceutical formulations comprising $T_3S$ as an active principle, as such or in combination with other thyroid hormones or pro-hormones. Particularly preferred are formulations comprising $T_3S$ in association with $T_4$.

Said formulations differ in the dosage of the active principle or principles, or in the type of pharmaceutical form provided, depending on the desired administration kind. Moreover they can also contain useful additives like excipients, diluents, dissolvents, solvents, carriers, dyestuffs, flavourings, sweeteners commonly used in the pharmaceutical technology. The preparation of specific pharmaceutical formulations in response to particular needs of administration is plainly comprised in the general technical field of the present invention.

EXPERIMENTAL SECTION

As an example, absolutely non-limiting for the skilled technician, $T_3S$ may be administered for oral use at doses ranging from 5 to 1000 µg, preferably from 10 to 500 µg, more preferably from 25 to 250 µg.

Analogously, when in association with $T_4$, preferred doses range from 10 to 500 µg for $T_3S$ and from 10 to 250 µg for $T_4$, more preferably from 25 to 250 µg for $T_3S$ and from 25 to 200 µg for $T_4$.

Two representative formulations for oral administration, selected among the preferred ones, are hereinafter enclosed by way of an example. Obviously, said formulations have no limiting effect on the other possible variations, which may also comprise different types of administration, different doses or different components depending on the specific pharmacological application or the particular pathology.

Example A

Oral Formulation Containing $T_3S$

| | |
|---|---|
| $T_3S$ | 50 µg; |
| Calcium phosphate dibasic anhydrous | 103.5 mg; |
| Mais starch | 17.65 mg; |
| Microcrystalline cellulose | 5 mg; |
| Sodium carboxymethylamide | 5 mg; |
| Talc | 5 mg; |
| Citric acid | 2.8 mg; |
| Magnesium stearate | 1 mg |

Example B

Oral Formulation Containing $T_3S$ and $T_4$

| | |
|---|---|
| $T_3S$ | 50 µg; |
| $T_4$ sodium salt | 125 µg; |
| Calcium phosphate dibasic anhydrous | 103.5 mg; |
| Mais starch | 17.525 mg; |
| Microcrystalline cellulose | 5 mg; |
| Sodium carboxymethylamide | 5 mg; |
| Talc | 5 mg; |
| Citric acid | 2.8 mg; |
| Magnesium stearate | 1 mg |

In particular, when the association is taken into account, the formulations of the present invention will also possibly comprise individually formulated doses of $T_3S$ and $T_4$, so that sequential administration is possible. In this case, one suitable kit is provided, which consents distinct administration of said active principles in ways that can differ from patient to patient, depending on the needed therapeutic application. In such a way, the specialized physician will have a wide choice of changing the prescription according to the actual need of the patient.

Just by way of an absolutely non-limitative example, in the case of oral administration, one package containing two individual blisters, which have different shape and/or color and/or different contents and/or doses, may suit the desired scope. Other possibilities exist and are easily available to the expert of the field.

The pharmaceutical compositions of the present invention are usable in the treatment of pathologies due to organic deficiency of triiodothyronine ($T_3$), like, for example, original hypothyroidism from autoimmune thyroid affections, hormonal production defects, thyroidectomy, congenital hypothyroidism, as well as some disorders due to reduced activity of type I 5'-iodothyronine monodeiodinase (type I MD) which is induced, for example, by hypothyroidism, non thyroidal systemic illnesses, fast, selenium shortage and so on.

REFERENCES

1. Chopra I J. Nature, source and relative biological significance of circulating thyroid hormones. In: Braverman L E., Utiger R D. (eds) The Thyroid, Lippincott, Philadelphia 1991, pp. 126-143.
2. Spaulding S W., Smith T J., Hinkle P M., Davis F B., Kung M P., Roth J A. Studies on the biological activity of triiodothyronine sulfate. J. Clin. Endocrinol. Metab. 1992, 74, 1062-1067.
3. Lo Presti J S., Mizuno L., Nimalysuria A., Anderson K P., Spencer C A., Nicoloff J T. Characteristics of 3,5,3'-triiodothyronine sulfate metabolism in euthyroid man. J. Clin. Endocrinol. Metab. 1991, 73, 703-709.
4. Santini F., Hurd R E., Chopra I J. A study of metabolism of deaminated and sulfoconjugated iodothyronines by rat placental iodothyronine 5-monodeiodinase. Endocrinology 1992, 131, No. 4, 1689-1694.
5. Otten M H., Mol J A., Visser T J. Sulfation proceding deiodination of iodothyronines in rat hepatocytes. Science 1983, 221, 81-83.
6. Mol J A., Visser T J. Rapid and selective inner ring deiodination of $T_4$ sulfate by rat liver deiodinase. Endocrinology 1986, 117, 8-12.
7. Kung M P., Spaulding S W., Roth J A. Desulfation of 3,5,3'-triiodothyronine sulfate by microsomes from human and rat tissues. Endocrinology 1988, 122, 1195-1200.
8. Santini F., Chopra I J., Wu S Y., Solomon D H., Chua Teco G N. Metabolism of 3,5,3'-triiodothyronine sulfate by tissues of the fetal rat: a consideration of the role of desulfation of 3,5,3'-triiodothyronine sulfate as a source of $T_3$. Pediatr. Res. 1992, 31, 541-544.
9. De Herder W W., Hazenberg M P., Pennock-Schroeder A M., Hennemann G., Visser T J. Rapid bacteria-dependent in vitro hydrolysis of iodothyronine conjugates by intestinal contents of humans and rats. Med. Biol. 1986, 64, 31-35.
10. Santini F., Hurd R E., Lee B., Chopra I J. Thyromimetic effects of 3,5,3'-triiodothyronine sulfate in hypothyroid rats. Endocrinology 1993, 133, No. 1, 105-110.
11. Santini F., Chiovato L., Ghiri P., Lapi P., Mammoli C., Montanelli L., Scartabelli G., Ceccarini G., Coccoli L., Chopra I J., Boldrini A., Pinchera A. Serum iodothyronines in human fetus and the newborn: evidence for an important role of placenta in fetal thyroid hormone homeostasis. J. Cl. Endocrinol. Metab. 1999, 84, No. 2, 493-498.
12. Santini F., Pinchera A., Ceccarini G., Castagna M., Rosellini V., Mammoli C., Montanelli L., Zucchi V., Chopra I J., Chiovato L. Evidence for the role of the type III-iodothyronine deiodinase in the regulation of 3,5,3'-triiodothyronine content in the human central nervous system. Eur. J. Endocrinol. 2001, 144, 577-583.
13. Santini F., Cortellazzi D., Baggiani A M., Marconi A M., Beck-Peccoz P., Chopra I J. A study of the serum 3,5,3'-triiodothyronine sulfate concentration in normal and hypothyroid fetuses at various gestational stages. J. Cl. Endocrinol. Metab. 1993, 76, No. 6, 1583-1587.
14. Chopra I J., Nguyen D. Demonstration of thyromimetic effects of 3,5,3'-triiodothyronine sulfate ($T_3S$) in Euthyroid rats. Thyroid 1996, 6, No. 3, 229-232.

The invention claimed is:

1. A solid composition comprising triiodothyronine sulfate_at a dose ranging from 5 to 1000 µg together with pharmaceutically acceptable additives for oral administration to a human as a thyroid hormone substitute therapy.

2. The composition according to claim 1, comprising triiodothyronine sulfate at a dose ranging from 10 to 500 µg.

3. The composition according to claim 2, further comprising from 10 to 250 µg of thyroxine.

4. The composition according to claim 2, comprising triiodothyronine sulfate at a dose ranging from 25 to 250 µg.

5. The composition according to claim 3, further comprising from 25 to 200 µg of thyroxine.

6. A kit comprising (i) a solid composition according to claim 2 and ((ii) a solid composition comprising an effective amount of thyroxine for oral administration to a human.

7. The kit according to claim 6, comprising from 10 to 500 µg of triiodothyronine sulfate and from 10 to 250 µg of thyroxine, in compositions (i) and (ii), respectively.

8. The kit according to claim 7, comprising from 25 to 250 µg of triiodothyronine sulfate and from 25 to 200 µg of thyroxine, in compositions (i) and (ii), respectively.

9. A method of treating a subject with a pathology due to organic deficiency of triiodothyronine comprising oral administration of a solid composition according to claim 1.

10. The method according to claim 9, wherein the triiodothyronine sulfate is administered at a dose ranging from 10 to 500 µg.

11. The method according to claim 10, wherein the triiodothyronine sulfate is administered at a dose ranging from 25 to 250 µg.

12. A method of treating a subject with a pathology due to organic deficiency of triiodothyronine comprising oral administration of a solid composition according to claim 3.

13. The method according to claim 12, wherein the triiodothyronine sulfate is administered at a dose ranging from 25 to 250 μg and the thyroxine is administered at a dose ranging from 25 to 200 μg.

14. The method according to any one of claim 9 or 12, wherein said pathology is selecetd from the group consisting of original hypothyroidism from autoimmune thyroid affections, hormonal production defects, thyroidectomy, and congenital hypothyroidism.

15. The method according to any one of claim 9 or 12, wherein said pathology is due to reduced activity of type I 5'-iodothyronine monodeiodinase.

16. The method according to claim 15, wherein said reduced activity of type I 5'-iodothyronine monodeiodinase is due to hypothyroidism, non thyroidal systemic illness, fast, or selenium shortage.

* * * * *

UNITED STATES PATENT AND TRADEMARK OFFICE
CERTIFICATE OF CORRECTION

PATENT NO.       : 9,012,438 B2
APPLICATION NO.  : 10/532447
DATED            : April 21, 2015
INVENTOR(S)      : Pinchera et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 151 days.

Signed and Sealed this
Twenty-first Day of June, 2016

Michelle K. Lee
*Director of the United States Patent and Trademark Office*